United States Patent

Hudson et al.

[11] Patent Number: 6,100,024
[45] Date of Patent: *Aug. 8, 2000

[54] METHODS AND COMPOSITIONS FOR NUCLEIC ACID DETECTION BY TARGET EXTENSION AND PROBE AMPLIFICATION

[75] Inventors: Geoffrey R. Hudson; James W. Schumm; Randall L. Dimond, all of Madison, Wis.

[73] Assignee: Promega Corporation, Madison, Wis.

[*] Notice: This patent is subject to a terminal disclaimer.

[21] Appl. No.: 07/652,888

[22] Filed: Feb. 8, 1991

[51] Int. Cl.[7] .............................. C12Q 1/68; C07H 21/04
[52] U.S. Cl. ..................... 435/6; 435/91.2; 536/23.1; 536/24.1; 536/24.3; 536/24.31; 536/24.32; 536/24.33; 935/77; 935/78
[58] Field of Search .............. 435/6, 91, 172.3, 435/91.2; 536/18.7, 23.1, 24.33, 24.1, 24.2, 24.3–24.32; 935/2, 9, 17, 18, 19, 78, 88

[56] References Cited

U.S. PATENT DOCUMENTS

| | | | |
|---|---|---|---|
| 4,786,600 | 11/1988 | Kramer et al. | 435/235 |
| 4,957,858 | 9/1990 | Chu et al. | 435/6 |
| 5,112,734 | 5/1992 | Kramer et al. | 435/6 |
| 5,118,801 | 6/1992 | Lizardi et al. | 536/27 |
| 5,356,774 | 10/1994 | Axelrod et al. | 435/6 |

FOREIGN PATENT DOCUMENTS

| | | |
|---|---|---|
| 8410413 | 11/1989 | WIPO. |
| 9001068 | 2/1990 | WIPO. |
| 9002819 | 3/1990 | WIPO. |
| 9002820 | 3/1990 | WIPO. |

OTHER PUBLICATIONS

Blumenthal et al. (1979) Annual. Rev. of Biochemistry, vol. 48, pp. 525–548.

Gulati et al. P.N.A.S. 71(4):1035 (1974).

Miele et al. J. Mol. Biol. 171:281 (1983).

Weier et al. Nucl. Acid. Res. 16(24):11836 (1988).

Chu et al. Nucl. Acids Res. 14(14):5591 (1986).

Sharmeen et al. Nucleic Acids Res. 15(16):6705 (1987).

Milligan et al. Nucleic Ad. Res. 15(21):8783 (1987).

Biebricher (1987) Cold Spring Harbor Symposia on Quantitative Biology, vol. 52, pp. 299–306.

Engelke et al. (1988) Proc. Natl Acad Sci (USA), vol. 85, pp. 544–548.

*Primary Examiner*—Ardin H. Marschel
*Attorney, Agent, or Firm*—Foley & Lardner

[57] ABSTRACT

The present invention provides a novel, single-stranded DNA probe which comprises an anti-target segment, a strand of a promoter, and a reporter segment, arranged so that a target segment, which has a 3'-hydroxyl at its terminus, can prime DNA polymerase-catalyzed extension of the target segment along the probe as template, when the target segment is hybridized to the anti-target segment of the probe, to provide an extension product from which transcripts, with the sequence complementary to that of the reporter segment of the probe, can be made by transcription from the promoter corresponding to the promoter segment of the probe. The transcripts, optionally after further amplification or other processing, can be detected. In one embodiment of the invention, the transcripts will be autocatalytically replicatable by an RNA replicase such as Qβ replicase. The invention also provides methods of using a probe of the invention in testing a sample of nucleic acid for the presence of a nucleic acid which comprises target segment corresponding to the anti-target segment of the probe and test kits for carrying out such methods with a probe of the invention.

30 Claims, 3 Drawing Sheets

Transcriptional Autoamplifying Probe for Hepatitis B Virus (HBV)

Hepatitis B Virus (HBV) Probe With Reporter Segment Encoding Autocatalytically Replicatable RNA Transcriptional Autoamplifying Probe for Hepatitis B Virus (HBV)

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 129 bases
       (B) TYPE: nucleic acid
       (C) STRANDEDNESS: single
       (D) TOPOLOGY: linear (ii) MOLECULE TYPE: other nucleic acid (synthetic DNA)

(xi) SEQUENCE DESCRIPTION: SEQ ID NO:1:

GGGTTGACCC GGCTAGATCC GGGTGTGTCC TCTCTAACTT TCGAGTAGAG         50

AGGTGAGAAA ACCCCGTTAT CCTGGTAACA GGATTTCCCC TATAGTGTCA        100

CCTAAATTTC ACCTCTGCCT AATCATCTC                               129

(2) INFORMATION FOR SEQ ID NO:2:

(i) SEQUENCE CHARACTERISTICS:
       (A) LENGTH: 64 bases
       (B) TYPE: nucleic acid
       (C) STRANDEDNESS: single
       (D) TOPOLOGY: linear (ii) MOLECULE TYPE: other nucleic acid (synthetic DNA)

(xi) SEQUENCE DESCRIPTION: SEQ ID NO:2:

TTCACCTCTG CCTAATCATC TCTTCTATAG TGTCACCTAA ATTTCACCTC         50

TGCCTAATCA TCTC                                               64

(2) INFORMATION FOR SEQ ID NO:3:

(i) SEQUENCE CHARACTERISTICS:
       (A) LENGTH: 25 bases
       (B) TYPE: nucleic acid
       (C) STRANDEDNESS: single
       (D) TOPOLOGY: linear (ii) MOLECULE TYPE: other nucleic acid (RNA)

(ix) FEATURE: Transcript from bases 1-25 of SEQ ID NO:2
             when transcribed from the SP6 promoter, the
             template strand of which is bases 26-42 of
             SEQ ID NO:2.

(xi) SEQUENCE DESCRIPTION: SEQ ID NO:3:

GAAGAGAUGA UUAGGCAGAG GUGAA                                   25

(2) INFORMATION FOR SEQ ID NO:4:

(i) SEQUENCE CHARACTERISTICS:
       (A) LENGTH: 40 bases
       (B) TYPE: nucleic acid
       (C) STRANDEDNESS: single
       (D) TOPOLOGY: linear (ii) MOLECULE TYPE: other nucleic acid (synthetic DNA)

(xi) SEQUENCE DESCRIPTION: SEQ ID NO:4:

TGCACAGCTG GATCCTCTAG AGGCCTAGGG CCCCTCGAGC                    40

```
(2) INFORMATION FOR SEQ ID NO:5:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:5:

TATAGTGAGT CGTATTA                                                           17

(2) INFORMATION FOR SEQ ID NO:6:

(i) SEQUENCE CHARACTERISTICS:
        (A) LENGTH: 148 bases
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:6:

TGGGTTGACC CGGCTAGATC CGGGTGTGTC CTCTCTAACT TTCGAGTAGA                       50

GAGGTGAGAA AACCCCGTTA TCCTGGTAAC AGGATTCTCC CTATAGTGAG                      100

TCGTATTATG CACAGCTGGA TCCTCTAGAG GCCTAGGGCC CCTCGAGC                        168

(2) INFORMATION FOR SEQ ID NO:7:

(i) SEQUENCE CHARACTERISTICS:
        (A) LENGTH: 132 bases
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:7:

GGGTTGACCC GGCTAGATCC GGGTGTGTCC TCTCTAACTT TCGAGTAGAG                       50

AGGTGAGAAA ACCCCGCCGT TATCCTGGTA ACAGGATTTC CCCTATAGTG                      100

TCACCTAAAT TTCACCTCTG CCTAATCATC TC                                         132
```

METHODS AND COMPOSITIONS FOR NUCLEIC ACID DETECTION BY TARGET EXTENSION AND PROBE AMPLIFICATION

TECHNICAL FIELD

The present invention relates generally to nucleic acid probes, methods of using the probes in nucleic acid probe hybridization assays of samples of nucleic acid for nucleic acid analyte, and test kits for carrying out such methods.

BACKGROUND OF THE INVENTION

Nucleic acid probe hybridization assay technology is based on nucleic acid hybridization, i.e., the binding, through complementary base-pairing, of a nucleic acid strand with a strand of complementary, or nearly complementary, sequence to form a stable, doublestranded hybrid. Such hybridization can be made to occur between an RNA segment and a DNA segment, two RNA segments or two DNA segments, provided they have complementary or nearly complementary nucleotide sequences. Under suitable conditions (i.e., sufficiently high stringency), nucleic acid hybridization is highly specific, requiring exact complementarity in strands eight or more bases in length for stable binding. Nucleic acid hybridization provides a means for detecting DNA or RNA segments of specific sequence with great accuracy and sensitivity. A nucleic acid segment, if modified appropriately to be made detectable, may be used to "probe" for, and detect, its complementary segment.

Nucleic acid probe technology, relying upon hybridization of nucleic acid segments with complementary sequences, is recognized as having a powerful analytical and diagnostic potential. Because unique nucleic acid sequences distinguish all forms of life, including viruses and viroids, the specificity of hybridization reactions may be used to detect and diagnose infectious or genetic diseases or cancer, identify viral or microbial contaminants in a source or sample, such as food or water, identify cells or organisms, or identify or characterize individuals at the genetic level, for forensic or paternity testing in humans, or breeding analysis in plants and animals. For example, a disease, such as an infectious disease, genetic disorder or a cancer, will have specific, characteristic DNA or RNA sequences associated with it. The presence of such a characteristic sequence in a sample of cells can be detected with a nucleic acid probe, which includes a segment with a sequence complementary to that of the characteristic sequence. However, as yet, only a handful of nucleic acid probe-based tests has become routine in clinical diagnostic or screening applications.

A major problem attendant application of nucleic acid probe technology is the sensitivity of the assays. In many cases, it is necessary to detect accurately the presence of only a minute quantity of a target nucleic acid (nucleic acid analyte) in an enormous background of other nucleic acids. For example, a nucleic acid probe-based test or assay for detection of a disease-causing virus in a sample of human blood may require sufficient sensitivity and specificity to detect as little as a single molecule of target among a myriad of other nucleic acids. Sensitivity of assays depends on the ability of a probe to bind to a target molecule, the magnitude of the signal that is generated by each hybridized probe, and the time period available for detection.

Several approaches have been advanced for accomplishing reliable detection of target nucleic acid present in a test sample using nucleic acid probes. The development of suitable signal-generation systems represents one such approach. In such systems, the probe is labeled with a reporter group which may be an atom, functional group, or other moiety, such as a biotinyl group, a protein or a segment of nucleic acid, which is capable of producing, directly or indirectly, a detectable signal uniquely associated with the probe.

The simplest of such signal-generation methods includes, for example, $^{32}$P-radiolabeling of phosphate groups in the probe or covalent attachment of a fluorescent organic moiety to one of the bases in a probe or a nucleotide outside the segment of the probe that hybridizes to target. After hybridization of the labeled probe and separation of any unhybridized probe from the hybridized, the probe-target hybrids are detected by measuring radioactive decay or fluorescence, respectively. Such methods involve generation of signal by individual reporter groups and, as such, are fundamentally limited because of the number of reporter groups needed in a sample to produce a detectable signal that is distinguishable over background. The practicable lower detection limit for such methods is about $10^5$ target molecules. Much effort is therefore being expended in increasing the sensitivity of detection systems for nucleic assay probe hybridization assays.

Signal or reporter amplification methods have been developed as another approach to increasing sensitivity of detection systems for nucleic assay probe hybridization assays. Such methods involve amplification of a label attached to a probe. Such a label is typically a moiety which is capable of catalyzing a reaction. After the probe is introduced into a test sample under conditions which allow the probe to hybridize with any target segment and separated from any unhybridized probe, the hybridized probe is subjected to conditions which allow the catalysis to proceed. As a result a large number of detectable molecules is made for each molecule of probe that hybridized to target nucleic acid. For example, an enzyme such as alkaline phosphatase or a peroxidase, is linked to a probe and, after probe hybridization and separation of hybridized from any unhybridized probe, is incubated, under conditions suitable for activity of the enzyme, with a specific chromogenic substrate to produce a large number of a characteristic colored molecules for each probe molecule that hybridized to target. Linkage of enzyme to probe can be prior to hybridization, e.g., through a covalent linker to a functional group in the nucleic acid of the probe, or after hybridization and separation, e.g., through complexing to a biotinyl moiety, which is covalently linked to a nucleotide of the probe, and then to a complex of avidin and the enzyme. While such signal amplification systems provide improvement in sensitivity over simpler non-radioactive reporter systems that do not employ signal amplification, they are typically 10 to 100 times less sensitive than signal-generation systems based on $^{32}$p-labeling and are often cumbersome and time-consuming to carry out.

A reporter amplification system has been described recently which exhibits vastly improved sensitivity. This system utilizes as a reporter group an RNA which is susceptible to autocatalytic replication. See, for example, Blumenthal and Carmichael (1979), Ann. Rev. Biochem. 48:525–548; Chu et al., PCT Patent Publication No. WO 87/06270; Feix and Sano (1976) FEBS Letters 63:201–204; Kramer and Lizardi (1989) Nature 339:401–402; Kramer et al., U.S. Pat. No. 4,786,600; Lizardi et al. (1988) Biotechnology 6:1197–1202; and Schaffner et al. (1977), J. Mol. Biol. 117:877–907. One such reporter moiety is a replicatable RNA, which serves as a template for replication catalyzed by an RNA-directed RNA polymerase (an RNA replicase), such as Qβ-replicase. In this system, the replicatable RNA is covalently joined to the probing segment (anti-target segment)(i.e., the segment that hybridizes to target segment in nucleic acid analyte) of a probe. After probe hybridization with target and separation of hybridized from unhybridized probe, the replicatable RNA (as part of the probe or after separation therefrom) is incubated with ribonucleotide triphosphates and the replicase, which catalyzes autocatalytic replication of the replicatable RNA, to produce up to about $10^6$ copies of such an replicatable RNA for each probe molecule that was hybridized to target analyte. Such amplification can be made in about 10 to 12 minutes.

Another approach that has been taken to improve the sensitivity of detection of target nucleic acids with nucleic acid probes involves direct or indirect amplification of a segment of the target nucleic acid, so that the segment reaches a quantity sufficient to be readily detectable using currently available signal-generation and signal-detection methods. Traditional examples of this approach are the various subculturing techniques, in which cells that harbor the target segment are selected and caused to increase in number or are treated to cause nucleic acid, which comprises the target segment, to replicate to high copy number. See, for example, Lennette et al. (1985), Manual of Clinical Microbiology, American Society for Microbiology, Washington, D.C.; Gerhardt, P. (1981), Manual of Methods for General Bacteriology, American Society for Microbiology, Washington, D.C. Such techniques are typically cumbersome and time-consuming and often increase the non-target nucleic acids of the background as well as target.

Recent advances in the target amplification approach have focused on selective, target-dependent increases of target segment or its complement (i.e., a nucleic acid segment of complementary sequence). One such method is the now well known "polymerase chain reaction" (PCR) method. See, e.g., Erlich (Ed.) (1989), PCR Technology, Stockton Press, New York, N.Y.; Erlich et al. (1988) Nature, 331:461–462; Mullis and Faloona (1987) Methods in Enzymology, 155:355–350; Saiki et al. (1986) Nature, 324:163–166; Saiki et al. (1988) Science, 239:487–491; Saiki et al. (1985) Science, 230:1350–1354; and Mullis et al., U.S. Pat. No. 4,683,195, and Mullis, U.S. Pat. No. 4,683,202, both of which are incorporated herein by reference.

In the PCR method, a double-stranded target DNA is thermally denatured, and hybridized to a pair of primers which flank the segment of interest in the target, one primer with the sequence complementary to that of a subsegment at the 3' end of the target segment and the other with the same sequence as a non-overlapping subsegment at the 5' end of the target segment. The annealed primers are then extended by a DNA polymerase-catalyzed chain extension reaction using target and its complement as templates. After numerous (e.g., typically twenty-five) cycles of denaturation, hybridization and primer extension, a suitable level of amplification of target segment may be achieved. In a twenty-five cycle PCR process, about $10^6$ target segments can be generated for each target molecule present initially in a sample. A disadvantage of the PCR technique is the many cycles of denaturation, hybridizing and primer-extension that are required for suitable levels of amplification in virtually all practical applications. Additionally, the amplification process is more time-consuming if carried out manually and quite expensive if automated.

A transcription-based technique for target amplification has also been described. See Gingeras et al., PCT Patent Publication No. WO 88/10315. This technique, referred to as the transcription-based amplification system (TAS), is based on the synthesis of a double-stranded DNA which comprises a target segment of nucleic acid analyte (target nucleic acid) operably linked for transcription to a promoter, which is recognized specifically by a DNA-dependent RNA polymerase (typically that of bacteriophage T3, bacteriophage T7, or bacteriophage SP6). Transcription from the promoter using the cognate RNA polymerase of the promoter can produce quickly a large number of transcripts comprising a sequence complementary to that of the target segment. If the amount of RNA made in a first round of a TAS process is not suitable, this RNA can be employed to initiate a second round, the RNA resulting from the second round (which will comprise a segment with the same sequence as target segment) can be employed to initiate a third round, and so on, until a suitable level of RNA for detection by known reporter methods is achieved. While the TAS method uses fewer steps than PCR to achieve the same level of amplification, TAS requires two more enzymatic reactions than PCR and no time savings in comparison with PCR is claimed.

The PCR method may be combined with the TAS method. For example, a series of PCR cycles may be used to generate many copies of double-stranded DNA comprising a promoter operably linked for transcription to a target segment and RNA transcripts can then be made using such DNA.

The TAS method may also be combined with a reporter system employing autocatalytic replication of RNA using an RNA dependent RNA polymerase (i.e., an RNA replicase). Essentially, the double-stranded DNA, that is prepared with target segment and includes a promoter to drive transcription from the DNA of an RNA which comprises a segment complementary to that of target segment, is constructed with suitable primers so that this RNA is autocatalytically replicatable by an RNA replicase. Typically, this RNA will be a known, autocatalytically replicatable RNA into which a segment with the sequence complementary to that of target segment has been inserted, at a site where the insertion can be tolerated without eliminating autocatalytic replicatability. See, e.g., Kramer et al., U.S. Pat. No. 4,786,600. After the transcript is made per the TAS method, the transcript is autocatalytically replicated using a replicase that recognizes the transcript as a template for autocatalytic replication. The RNAs resulting from the autocatalytic replication are then detected by known methods.

SUMMARY OF THE INVENTION

The present invention provides a novel, single-stranded DNA probe which comprises an anti-target segment, a strand of a promoter, and a reporter segment, arranged so that a target segment, which has a 3'-hydroxyl at its terminus, can prime DNA polymerase-catalyzed primer extension ("chain extension") of the target segment along the probe as template, when the target segment is hybridized to the anti-target segment of the probe, to provide an extension product from which transcripts, with the sequence complementary to that of the reporter segment of the probe, can be made by transcription from the promoter corresponding to the promoter segment of the probe. The transcripts, optionally after further amplification or other processing, can be detected by any of numerous techniques well known to the skilled. In one embodiment of the invention, the transcripts will be autocatalytically replicable by an RNA replicase such as Qβ replicase. In another embodiment, the transcripts will comprise a segment (preferably at the 3'-end of the transcript) with the same sequence as target segment, so that the transcripts themselves can prime production of double-stranded DNA to produce more transcript. The invention also provides methods of using a probe of the invention in testing a sample of nucleic acid for the presence of a nucleic acid analyte (target nucleic acid) which comprises target segment corresponding to the anti-target segment of the probe and test kits for carrying out such methods with a probe of the invention.

DETAILED DESCRIPTION

Figure 1:
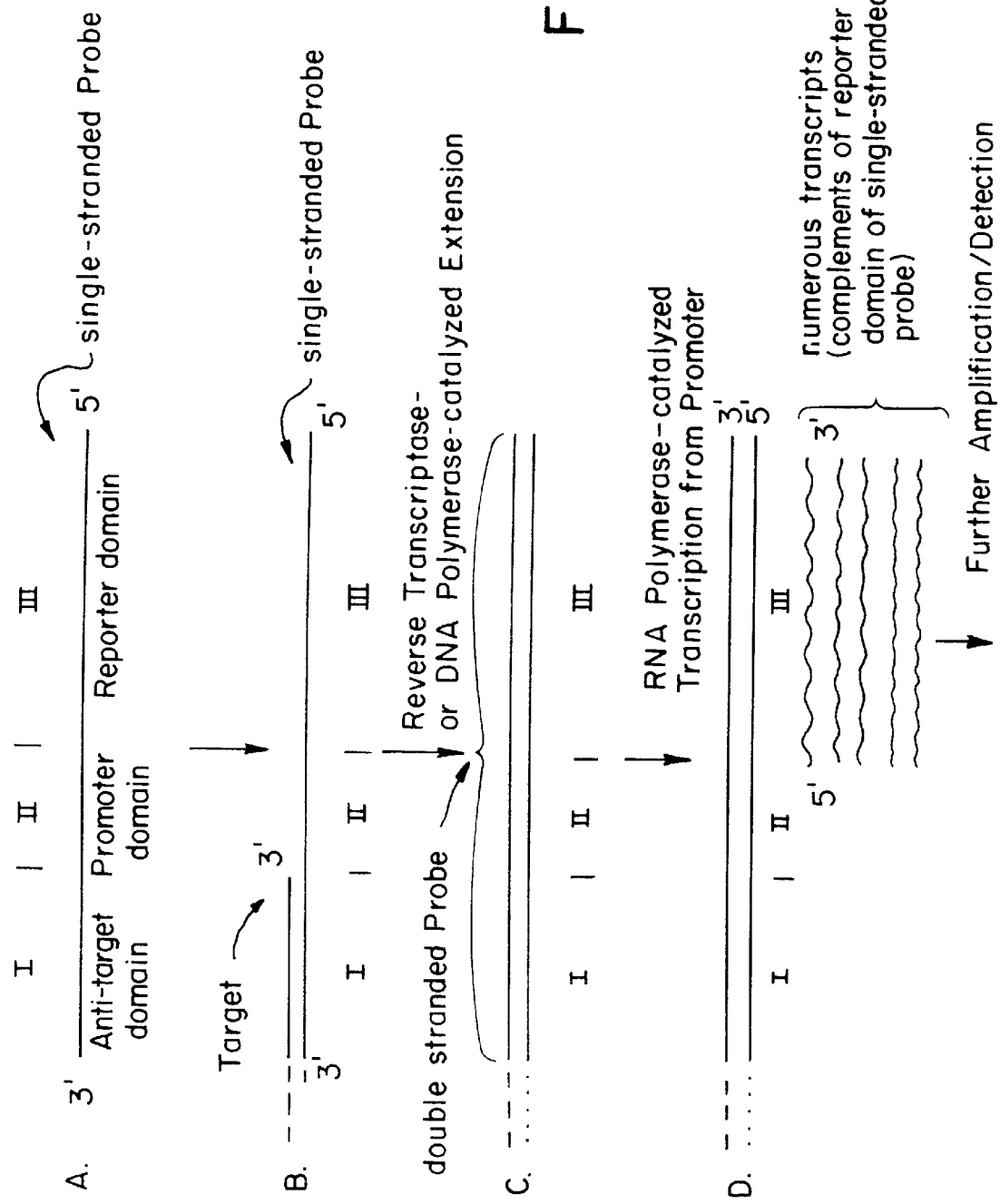
FIG. 1 illustrates a probe of the invention and the steps of a method of the invention for target-dependent amplification of the probe via production of transcripts from a double-stranded DNA made by chain-extension of the target segment of the target hybridized to probe. The Figure also illustrates that the transcripts can be detected, optionally after further amplification, to provide a method for detecting nucleic acid analyte which comprises target segment to which probe, via its anti-target segment, is capable of hybridizing in a way that allows priming by the target segment of chain extension catalyzed by a DNA polymerase and using probe as template. Step A details the construction of a single-stranded probe of the present invention which may be added to the sample to be analyzed. Step B illustrates the hybridization of the single-stranded probe to the target nucleic acid. Step C shows extension of the target nucleic acid resulting in the formation of a double-stranded promoter. Step D illustrates the amplification of the reporter domain of the single-stranded probe.

In the following description, unless otherwise indicated, process steps are carried out and concentrations are measured at room temperature (about 20° C. to about 25° C.) and atmospheric pressure.

In one of its aspects, the invention is a DNA probe, which has (a) a first segment, which is an anti-target segment, by which the probe can hybridize to a target segment of a target nucleic acid in a sample (typically an aqueous solution) of nucleic acid, and (b) a second segment (1) which can serve as a template for a DNA-dependent DNA polymerase-catalyzed primer extension reaction from target segment hybridized to the anti-target segment, when the target segment is at the 3'-end of a nucleic acid segment and has a 3'-hydroxyl group, and (2) which comprises a segment that is the strand of a promoter and a segment that is a "reporter segment", with said promoter segment and reporter segment positioned and oriented with respect to each other such that, with the double-stranded DNA resulting from the primer extension of the target segment hybridized to the anti-target segment of the probe, an RNA polymerase that recognizes the promoter corresponding to the promoter segment can be used to catalyze transcription to yield a transcript with the sequence complementary to that of the reporter segment.

In other aspects, the invention entails a method for detecting the presence of a target nucleic acid, which comprises a target segment, in a sample of nucleic acids which method comprises treating the target nucleic acid, if necessary, to provide target segment at the 3'-end of nucleic acids and having a 3'-hydroxyl group, hybridizing to such target segment probe of the invention which has an antitarget segment to permit such hybridization, chain-extending the target segment so hybridized in a reaction catalyzed by an enzyme with DNA-dependent DNA polymerase activity to form a double-stranded DNA segment, one strand of which is the second segment of the probe, catalyzing transcription from said double-stranded DNA segment using a DNA-dependent RNA polymerase that recognizes the promoter in the segment for initiation of transcription, and, optionally after amplification of the transcript so made, detecting the production of such transcript.

In still another aspect, the invention entails test kits for carrying out the methods of the invention for detecting the presence of target nucleic acid in a sample of nucleic acid.

With more particularity, then, the invention, in one aspect, is a nucleic acid probe, for detection of a preselected target nucleic acid segment which has an hydroxyl group at its 3'-terminus, said probe comprising a first segment and a second segment, (a) said first segment being a DNA segment or an RNA segment and having the same number of nucleotides as said target segment and having a sequence whereby said target segment is capable of hybridizing to said first segment and, when so hybridized, priming chain extension which provides a double-stranded DNA segment of which one strand is said second segment; and (b) said second segment comprising:
   (i) a third segment, which is the (−)-strand of a promoter;
   (ii) a first linker between said first and third segments, said first linker being a bond, or a fourth segment of one or more nucleotides, between the 3'-carbon of the 3'-terminal nucleotide of the third segment and the 5'-phosphate of the 5'-terminal nucleotide of the first segment;
   (iii) a fifth segment, which is a reporter segment; and
   (iv) a second linker between said third and fifth segments, said second linker being a bond, or a sixth segment of one or more nucleotides, between the 3'-carbon of the 3'-terminal nucleotide of the fifth segment and the 5'-phosphate of the 5'-terminal nucleotide of the third segment;

provided that said second segment is functional as a template for catalysis, by an enzyme with DNA polymerase activity, of DNA synthesis, primed by said preselected target segment hybridized to the nucleic acid probe, and that, in double-stranded DNA, one strand of which comprises, in the same order as in the DNA probe, said first, third and fifth segments and said first and second linkers, a segment comprising said fifth segment is capable of being transcribed, under control of the promoter corresponding to said third segment, to yield a transcript comprising a segment with the sequence complementary to that of said fifth segment.

As the skilled will understand, the first segment of a probe of the invention must be of length and sequence whereby the segment is capable of hybridizing to target segment with sufficient stability to permit the target segment to prime a chain-extension reaction using the second segment of the probe as template. Further, it is desirable that the first segment be of a length and sequence to provide specificity to binding between probe and nucleic acid of a sample being analyzed. As a practical matter, 6 nucleotides will be the minimum length of first segment in probes used in practical applications.

The first linker, joining first and second segments of a probe of the invention, can be a bond or can be any moiety which does not prevent formation in the primer extension reaction from target segment hybridized to probe of the double-stranded DNA, of which one strand is the second segment of the probe. Typically the linker will be a bond or a short segment of nucleotides.

The third segment of a probe of the invention (promoter segment)is designated the "(−)" strand of a promoter, by which is meant the template strand, i.e. the strand of the promoter which is part of the same strand as the DNA segment, of which has the sequence complementary to that of the transcript from the promoter. As should be apparent from the description herein, the third segment of the probe is located nearer the 3'-end of the probe than the reporter segment.

The fifth segment of a probe of the invention (reporter segment) is the segment with the sequence complementary to that of the transcript that is made, if probe hybridized to target segment so that double-stranded DNA from which the transcription could occur was formed. Thus, the fifth segment "reports" the hybridization of probe to target segment and subsequent primer extension of target segment to provide a double-stranded DNA segment from which transcripts can be made. The nucleotide at the 3'-end of the segment designated the fifth segment is the complement of the nucleotide (ribonucleotide) at the 5'-end of the transcript. Thus, the 3'-end of the fifth segment corresponds to the transcriptional start site in the double-stranded DNA made by primer extension from target segment hybridized to probe. Typically, the second linker joining the third and fifth segments of a probe of the invention will be simply a bond, although it may, with some promoters as third segment, be a segment of nucleotides or any other moiety which does not interfere with formation of the double-stranded DNA or transcription from the promoter of such double-stranded DNA.

As the skilled will understand, the fifth segment will have a sequence and length to make the corresponding transcript suitable for detection, in the system in which such detection must be carried out and by the method of detection that is employed.

Usually, the first segment of a probe of the invention, and the entire probe, will consist of 2'-deoxyribonucleotides (i.e., be a DNA). The second segment of a probe of the invention will be a DNA segment, in order to function as a template for DNA-dependent DNA polymerase catalyzed chain-extension and to provide a double-stranded DNA from which transcription can occur.

Although, in a probe of the invention, there may be nucleotides located 3' from the 3'-end of the first segment and 5' from the 5'-end of the reporter segment, it is generally preferable, for ease of synthesis, to keep probes as short as possible. Thus, usually the 3'-end of the first segment of a probe will be the 3'-end of the probe and the 5'-end of the reporter segment of a probe will be the 5'-end of the probe. Preferred promoters for use in accordance with the invention are those recognized by the RNA polymerase of a bacteriophage selected from the group consisting of T3, T7 and SP6 phage. Numerous such promoters are known in the art.

A preferred reporter segment in a probe of the invention will have the sequence of an RNA that is a template for autocatalytic replication by an RNA replicase. Many such replicases are known in the art. The preferred replicase is Qβ replicase, the replicase of bacteriophage Qβ. Numerous templates for autocatalytic replication by the various replicases are known. Reference may be made, for example, to Chu et al., PCT Patent Publication No. WO 87/06270 for discussion of RNA replicases and templates for autocatalytic replication by the replicases. Thus, reporter segments with sequences of midivariant RNAs, nanovariant RNAs, and other RNAs autocatalytically replicatable by Qβ replicase can be used.

Reference herein to a DNA having the "same" sequence as an RNA, or an RNA having the "same" sequence as a DNA means that the base is the same at each position in the DNA and RNA, except a thymine at a position in the DNA corresponds to a uracil at the same position in the RNA.

Probes of the invention that are shorter than about 200 nucleotides in length can be made and purified by standard, automated, in vitro synthetic techniques and electrophoretic or chromatographic purification techniques readily available in the art. Probes that are longer than about 200 nucleotides can be prepared enzymatically, e.g., using polymerase-chain reaction based techniques, also as available in the art.

More particularly, in another of its aspects, the invention entails a method of testing a sample of nucleic acid for the presence of a target nucleic acid comprising a preselected target segment, said method comprising:

(a) combining nucleic acid of the sample with a DNA probe under conditions whereby, if the target nucleic acid is present in the sample, the probe anneals to the target segment, said probe comprising a first segment and a second segment, (i) said first segment having the same number of nucleotides as said target segment and having a sequence whereby said target segment is capable of hybridizing to said first segment and, when so hybridized, priming chain extension which provides a double-stranded DNA segment of which one strand is said second segment; and (ii) said second segment comprising:

(A) a third segment, which is the (−)-strand of a promoter;

(B) a first linker between said first and third segments, said first linker being a bond, or a fourth segment of one or more nucleotides, between the 3'-carbon of the 3'-terminal nucleotide of the third segment and the 5'-phosphate of the 5'-terminal nucleotide of the first segment;

(C) a fifth segment, which is a reporter segment; and (D) a second linker between said third and fifth segments, said second linker being a bond, or a sixth segment of one or more nucleotides, between the 3'-carbon of the 3'-terminal nucleotide of the fifth segment and the 5'-phosphate of the 5'-terminal nucleotide of the third segment;

(iii) provided that (A) said second segment is functional as a template for catalysis, by an enzyme with DNA polymerase activity, of DNA synthesis, primed by said preselected target segment, when said target segment is the 3'-terminal segment of a nucleic acid, has an hydroxyl group at its 3'-terminus, and is hybridized to the nucleic acid probe, and (B) in double-stranded DNA, one strand of which comprises, in the same order as in the DNA probe, said first, third and fifth segments and said first and second linkers, a segment comprising said fifth segment is capable of being transcribed, under control of the promoter corresponding to said third segment, to yield a transcript comprising a segment with the sequence complementary to that of said fifth segment;

(b) before or after step (a), treating nucleic acid of the sample so that at least a portion of target segment annealed to probe is the 3'-terminal segment of nucleic acids and has an hydroxyl group at its 3' terminus;

(c) combining with the product of steps (a) and (b) an enzyme with DNA polymerase activity under conditions whereby target segment, which is annealed to probe, is the 3'-terminal segment of nucleic acids, and has an hydroxyl group at its 3'-terminus, primes DNA synthesis along the second segment of probe as a template to yield a segment of double-stranded DNA, in which said second segment is one of the strands;

(d) combining with the product of step (c) an RNA polymerase, which recognizes for initiation of transcription the promoter of said segment of double-stranded DNA which is the product of step (c), under conditions whereby RNA, which comprises a segment with the sequence complementary to that of the fifth segment of the DNA probe, is transcribed from said segment of double-stranded DNA; and (e) ascertaining whether RNA, which comprises a segment with the sequence complementary to that of the fifth segment of the DNA probe, was produced in step (d).

Samples of nucleic acid analyzed by this method of the invention will usually be aqueous solutions of nucleic acid derived from a biological sample and separated by methods known in the art from materials, such as proteins, lipids, or the like, in a biological sample that may interfere with the method or significantly increase the "background" signal in carrying out the method. Biological samples which can be used as sources of nucleic acid for the method include samples of virtually any substance which includes nucleic acid, including blood, urine, saliva, sera, stools, cultures of microorganisms, milk that may be contaminated with a microorganism, food, cosmetics or water that may be contaminated with a microorganism, or the like, as appreciated in the art.

A sample of nucleic acid, to which the method of the invention is to be applied, is, if necessary, treated so that at least a portion of any target nucleic acid in the sample will be processed to provide target segment (or subsegments of target segment capable of hybridizing with anti-target segment of probe to prime chain extension thereon), with 3'-hydroxyl, at the 3'-ends of nucleic acid fragments of target. Note that in some cases, no such treatment may be required because target segment of target nucleic acid is selected to be at the 3'-end and have a 3'-hydroxyl. In any case, one method of such treatment is random cleavage by sonication or treatment with certain exonucleases. Another method involves incubation with one, or several, restriction endonucleases which produce cleavage products have 3'-hydroxyl ends. Numerous closely spaced restriction endonuclease cleavage sites within the target can ensure the quantitative exposure of a 3' hydroxyl terminus within the region desired when the appropriate enzymes are employed. Selecting more than one restriction enzyme can minimize the impact of silent base changes.

Another method of cleaving target to yield target segment at the 3'-end of nucleic acids and having a 3'-hydroxyl involves use of chiral metal complexes (such as those containing Cu, Fe, or Pb) to cleave DNA into fragments have the desired 3' hydroxyl ends. See, e.g., Le Doan et al., (1987) Nucleic Acids Res. 15:8643–8659; Kean et al. (1985) Biochemistry 24:5062–5070.

Under special circumstances, single-stranded DNA and RNA-DNA hybrids can be cut precisely and quantitatively. Nishigaki et al., Nucl. Acids Res. 13, 5747 (1985); Bischofberger et al., Nucl. Acids Res. 15, 709 (1987); Molloy et al., Nucl. Acids Res. 8,2939 (1980); New England Biolabs, Inc., 1988–89 Catalog, p. 133, Appendix. In this case, single-stranded nucleic acids are hybridized to nucleotide oligomers. RNA-DNA hybrids can be treated with RNase H to effect the specific degradation of the RNA moiety. Thus, ribonucleic acids with DNA oligomeric "clamps" hybridized at specific intervals will release the nonhybridized RNA sequences when digested with RNase H.

Similarly, single-stranded DNA can be cleaved at any location through the use of a restriction enzyme such as FokI and a DNA oligonucleotide clamp. FokI cuts double-stranded DNA a specific number of bases downstream from its palindromic recognition site. Thus, a clamp consisting of a sequence that folds back on itself to form the FokI recognition site and adjacent sequence which hybridizes with the target DNA, has been shown to promote the specific cleavage of single-stranded DNA in the presence of FokI. See Szybalski, Gene 40, 169 (1985); Podhajska and Szybalski, Gene 40, 175 (1985).

Another method involves the covalent attachment of photosensitive reagents to oligonucleotides which results in strand scission upon exposure of the hybrid to the appropriate conditions. See, Praseuth et al. J. Mol. Biol. 196, 939 (1987); Le Doan et al., Nucl. Acids Res. 15, 7749 (1987); Praseuth et al., Proc. Natl. Acad. Sci. (USA) 85, 1349 (1988). An alternative strategy, which minimizes the effects of mutations and deletions within the target nucleic acid, is to use a multiplicity of probes that are homologous to different highly conserved sequences within the target gene.

Ribonucleic acid targets are also amenable to amplification by the method according to the present invention. Strategies similar to those described above for DNA would result in the generation of unique target sequences with an available 3' hydroxyl end. As an example, a unique RNA ribosomal sequence can be excised from intact molecules by using oligodeoxyribonucleotides and RNase H. This molecule is then used to prime DNA synthesis on the probe by an enzyme with DNA-dependent DNA polymerase activity, such as Klenow Fragment of E. coli DNA Polymerase I or AMV reverse transcriptase. The latter enzyme has an endogenous RNase H activity, and in some cases can function in a one-step priming reaction of probe by target without the need for flanking oligodeoxyribonucleotides.

Targets, of course, can also be selected which have naturally occurring 3' ends in the target nucleic acid. Examples of this phenomenon include the nucleic acids of many viruses such as hepatitis, corona, polio, rabies, rota and human immunodeficiency viruses to name but a few. Furthermore, naturally occurring 3' ends are found on ribosomal and messenger ribonucleic acids. It is probable that each organism has ribonucleic acids with unique characteristics that can be exploited by the invention described herein. For example, in certain Campylobacter spp, ribosomal RNA has a discrete breakdown product which arises during purification and which can be visualized following electrophoresis. This observation suggests the possibility of specifically cleaving this RNA quantitatively at that site in the presence of protective ribosomal proteins. The resulting 3' terminus would be able to participate in primer extension.

Less specific methods exist for generating 3' termini in the sample nucleic acid. These include random cleavage by nucleases, physical shearing, treatment with chemicals such as acids or bases, and finally photoinduced cleavage in the presence of photosensitive reagents. The random cleavage promoted by nucleases can be focused to specific regions of the target nucleic acid by many methods. One example is the protection of specific nucleic acid tracts from nuclease digestion by interactive nucleic acid-binding proteins. Another method takes advantage of the specific substrate requirement of RNase H and consists of the mixed hybrid degradation of the RNA moiety catalyzed by RNase H. Similarly, there are many other RNases such as T1, T2, and CL3 that have specific sites of activity and may yield useful target fragments.

Once the nucleic acid of a sample to which the method of the invention is being applied has been treated to yield target segment at the 3'-end of nucleic acids and having 3'-hydroxyl, the sample is incubated in a manner sufficient to denature any double-stranded nucleic acid which may be present. This is typically accomplished by heating the sample. A suitable amount of the sample is then incubated with the probe. If the sample contains the desired target segment, the 3' end of the target segment is completely hybridized with the first segment of the probe at the 3' end of the probe, so that there are no unpaired bases at the 3'-terminus of the hybridized target. Unpaired 3' overhangs, however, will occur with more or less frequency depending on the method selected to fragment the target nucleic acid. Unpaired overhangs are more common when random fragmentation methods are employed. The unpaired 3' termini of the target nucleic acid in the probe-target hybrid can be resolved by the specific 3' to 5' exonuclease activities of, for example, Klenow Fragment or T4 DNA polymerase. The Klenow enzyme, however, has a relatively weak 3' to 5' single-stranded exonuclease activity and in instances where long overhangs are expected, the associated exonuclease functions of the T4 and T7 DNA polymerases, which are several thousand-fold stronger, may be utilized. Treatment of improperly positioned 3' target termini may require appropriate protection of the 3' end of the probe. Protection of the probe can be effected, for example, by including a single deoxyribonucleotide triphosphate in the reaction so that only single-stranded DNA is degraded while the enzyme polymerizes on double-stranded templates. Alternatively, the probe can have its phosphate backbone randomly substituted with alpha-phosphorothioate residues which are known to inhibit a broad spectrum of exonucleases.

After target is hybridized to probe the target may be processed to provide the target segment, with a 3'-hydroxyl, at the 3'-end of nucleic acid strands.

As the skilled will understand, the hybridization of the probe to the target nucleic acid is influenced by a number of parameters such as their respective concentrations, the extent of complementarity of the segments which are intended to hybridize. salt concentration, pH, time and temperature. The skilled are also aware that compositions other than the probe and target will be or may be present in the hybridizing reaction mix to, for example, facilitate hybridization, or as a consequence of the fragmentation procedure. Ideally, probe is added to the reaction in sufficient excess to drive the rapid binding of all available target segments.

After hybridization of probe with any target segment that may be in the sample being analyzed, target segment with 3'-hydroxyl annealed to first segment of probe is treated so that DNA synthesis along second segment of probe is primed from the target segment to yield a segment of double-stranded DNA, in which said second segment is one of the strands.

The target-probe hybrid is rendered double-stranded by the action of an enzyme with DNA-dependent DNA polymerase activity, of which many are known and readily available to the skilled. Suitable enzymes with such activity include Klenow Fragment (of *E. Coli.* DNA polymerase I), bacteriophage T4 DNA polymerase, bacteriophage T7 DNA polymerase, AMV reverse transcriptase and MMLV reverse transcriptase, Taq DNA polymerase, and many others.

The double-stranded DNA segments resulting from the primer extension reaction ("chain extension") if target nucleic acid was present in the sample being analyzed include a promoter oriented and positioned to make, in the presence of a suitable RNA polymerase recognizing the promoter and ribonucleoside triphosphates, a transcript with the sequence complementary to that of the fifth segment of the probe. The double-stranded promoter segment is fully functional. While the requirement for a double-stranded promoter is not absolute to yield transcript with the sequence complementary to that of the fifth segment of the probe, the level of transcription from single-stranded promoter sequences is many orders of magnitude less than is observed for a functional double-stranded promoter.

In accordance with the method, an RNA polymerase which recognizes the promoter is employed to catalyze transcription from any double-stranded DNA segment with the promoter that will be present in the sample if target was. Particularly preferred RNA polymerases are those from bacteriophage T7, bacteriophage SP6, and bacteriophage T3. Many promoters are known to the skilled for each of these RNA polymerases.

If excess RNA polymerase is added to the reaction, several enzyme molecules will successively initiate RNA synthesis at the promoter, and thus, the template supports multiple concurrent transcriptions along its length. When the RNA polymerase is added in excess, as many as 1,000 transcripts per template molecule are rapidly synthesized. Thus, these transcripts represent a 1,000-fold amplification of each initial hybridization of probe molecule with its unique target sequence.

In accordance with the detection method of the invention, after the transcription step, the sample is processed to ascertain whether transcription, indicating the presence of target nucleic acid in the sample at the time carrying out the method with the sample began, has occurred. Of course, as the skilled will understand, the method carried out on a sample must be carried out in conjunction with suitable controls in order to establish that any transcription that might be ascertained with the test sample was due to the presence in said test sample of nucleic acid analyte.

The multiple RNA transcripts which are generated as a result of the hybridization, target nucleic acid cleavage (if necessary), extension, and transcription reactions may be detected as reporter molecules by methods known in the art for detecting nucleic acids. Methods which would facilitate their detection include the incorporation of radioactively (or otherwise) labeled ribonucleoside triphosphates as substrates in the RNA polymerization, assays for a by-product of the RNA polymerization (such as pyrophosphate ($PP_i$)), or the binding of dyes such as acridine orange or ethidium bromide to the transcript.

Non-radioactively labeled ribonucleoside triphosphates that can be employed to label RNA made in the transcription step include such triphosphates that are labeled with biotin or iminobiotin, various fluorophores, or other readily detectable ligands. However, the use of these compounds (or radioactively labeled ones) requires a post-transcriptional separation step to separate incorporated from unincorporated, labeled ribonucleoside triphosphates. One method for accomplishing this separation is the selective precipitation of nucleic acids in the presence of cold trichloracetic acid (TCA). In another method, the transcripts can be selectively retained on DEAE-substituted matrices, or other solid supports bearing chemically linked affinity ligands, such as a complementary nucleic acid, to which the transcripts bind reversibly but the monomeric, unincorporated ribonucleoside triphosphates do not.

There are also alternatives for detection which do not require the separation of the transcripts from their monomeric precursors. Nucleic acids can selectively bind a number of dyes, and those dyes can be detected by standard means. For example, acridine orange fluoresces at 640 nm (nanometers) when it is electrostatically bound to the phosphate backbone of single-stranded nucleic acids. However, acridine orange exhibits a fluorescent shift to 530 nm when it is intercalated within a double-stranded molecule. Thus, if the transcript that is made were to have an extensive secondary structure, direct illumination of intercalated acridine orange would yield a characteristic fluorescence peak.

Assays for the other major end product of the transcription reaction, pyrophosphate, can also be effected without the necessity for separation. Sensitive enzymatic and chemical assays have been described for the spectrophotometric detection of pyrophosphate. A luminescent assay for pyrophosphate has also been reported. Nyren and Lundin, Anal. Biochem. 151, 504 (1985).

The sensitivity of pyrophosphate detection, and thus sensitivity of detection of the target nucleic acid by the method of the invention, can be enhanced by further amplifying the reporter RNA transcripts via secondary amplification.

The multiple RNA transcripts generated from the first hybridization, extension and transcription reaction can serve as intermediates for further amplification ("secondary amplification").

One secondary amplification technique which may be suitably employed with the method of the present invention involves having the first RNA transcript hybridized to the anti-target domain of a second probe molecule (which may have the same sequence as the first probe molecule) and has the potential for $10^4$ to $10^6$ fold amplification. This technique can be accomplished by having the fifth segment of the probe comprise, at its 5'-end, a subsegment with the same sequence as a subsegment (preferably of at least about 6 nucleotides) at the 5'-end of the first segment. See, e.g., FIG. 3. This technique requires no additional manipulation for hybridization, target extension, and transcription. These reactions may occur concurrently with the production of the initial transcripts within a single reaction tube.

Another suitable secondary amplification technique is a refinement of the secondary amplification described above. In this case, the first transcript is capable of acting as a target sequence and primes a second reaction on the first probe.

Yet another secondary amplification technique requires that a particular RNA transcript be made during the first amplification reaction. For example, the transcript may be any of the RNA templates which are replicated by Qβ-replicase, or other RNA replicases, in an autocatalytic manner. See PCT Patent Publication No. WO 88/10315 to Gingeras, et al., and Blumenthal and Carmichael (1979), Ann. Rev. Biochem., 48:525–548. Examples of such replicases that are suitable for use in the present invention include the Qβ-replicase and the Brome Mosaic Virus (BMV) as well as the alpha-virus replicases.

When such enzyme is present in the reaction medium during the process of transcription producing template for autocatalytic replication by the enzyme, the multiple transcripts that are produced during transcription can themselves undergo replication so as to exponentially increase the amount of RNA transcript produced. It has been shown that Qβ-beta replicase can generate $10^6$ copies of midivariant RNA in 12 minutes. Chu et al. (1986) Nucl. Acids Res. 14, 5591 1986). Therefore, by coupling this secondary amplification strategy with the first amplification, the potential exists for $10^8$ to $10^9$ fold amplification of the initial amount of target-probe hybrids suitable for primer extension and transcription.

Secondary amplification strategies are not limited to those described above. Another type of RNA transcript which could potentially be secondarily amplified is the so-called catalytic RNA. Cech, Science 236, 1532 (1987); Sharp and Eisenberg, Science 238, 729 (1987); Haseloff and Gerlach, Nature 334, 585 (1988). of particular interest are the RNAs which act as catalysts in the cutting and joining of other RNAs without undergoing any structural change. Thus, the product RNAs would further amplify the original catalytic RNA transcript signal.

Recently, an RNA has been reported to be the catalytic subunit of a polysaccharide branching enzyme Shevdova et al. Nucl. Acids Res. 15, 1745 (1987). This RNA is 31 nucleotides long and contains 10 modified bases such as those which are found in transfer RNA. By itself, this RNA has greater activity than the holoenzyme (RNA plus protein). Such a catalytically active RNA may be synthesized via the present invention. The reaction product of the catalytic reaction would be readily assayed, making it a useful detection product.

Reaction conditions for carrying out the various steps of methods in accordance with the invention are well known or easily ascertained by the skilled.

The invention also entails test kits for carrying out the assay methods of the invention. Such kits comprise, in one or more containers, usually conveniently packaged to facilitate use in assays, quantities of various compositions essential for carrying out the assays in accordance with the invention. Thus, kits comprise a DNA probe according to the invention. The kits may additionally comprises an enzyme with DNA polymerase activity, an RNA polymerase which recognizes, for initiation of transcription, the promoter corresponding to the third segment of the DNA probe of the kit, and reagents for processing the target nucleic acid to provide target segment as a 3'-terminal segment of nucleic acid having a 3'-hydroxyl group on the 3'-terminal nucleotide. The kits may also include reagents, including enzymes (e.g., Qβ replicase, for detecting transcripts made from the double-stranded DNA resulting from chain-extension of target segment hybridized to probe.

The test kits of the invention can also include, as well known to the skilled, various controls and standards, such as solutions of known target segment concentration, including no target segment (negative control) to ensure the reliability and accuracy of the assays carried out using the kits, and to permit quantitative analyses of samples of the analytes (e.g., target segment) of the kits.

The present invention is further explained by the following examples which should not be construed by way of limiting the scope of the invention in any manner.

EXAMPLE 1

A single-stranded DNA probe consisting of 132 nucleotides with the sequence SEQ ID NO:7 was synthesized on an automated DNA synthesizer (Model No. 380B, Applied BioSystems, Inc., Foster City, Calif., U.S.A.) The first segment of this probe (the probe's anti-target segment) includes the 3'-terminal nucleotide of the probe and is a 20-nucleotide segment with the same sequence as the segment of 20 nucleotides at the 3'-ends (including the 3'-terminal nucleotide) of the probes illustrated in FIGS. 2 and 3. The third segment (promoter segment) of the probe is the negative strand (i.e., template strand) of an SP6 RNA polymerase promoter having the sequence shown in FIGS. 2 and 3 and oriented, also as in FIGS. 2 and 3, so that the template for transcription from the promoter in the probe, when made double-stranded by chain-extension of target hybridized to probe, is the fifth segment of the single-stranded probe. The fifth segment (reporter segment) of the probe, at the 5'-end of the probe and including the 5'-terminal nucleotide, is a 93-nucleotide DNA with the sequence of an RNA that is a template for autocatalytic replication by Qβ-replicase. The sequence of the fifth segment differs from that of the segment shown as the "reporter segment" in FIG. 2 only by having the trinucleotide 5'-CCG added between nucleotides 63 and 64 of the probe shown in FIG. 2. For more information on the various segments, see later Examples hereinbelow. The first linker, joining the first and third segments of the probe, was a fourth segment, the dinucleotide 5'-TT. The second linker, joining the third and fifth segments of the probe, was a bond between the 5'-terminal phosphate of the third segment and the 3'-carbon of the 3'-terminal nucleotide of the fifth segment. To purify the probe, the full-length oligomer was electrophoresed on a 12% denaturing polyacrylamide-urea gel, visualized by UV shadowing, excised and recovered via gel electroelution (D-Gel® manufactured by EpiGene Co., Baltimore, Md., USA), and desalted using an ion exchange column (NAP-25® minicolumn manufactured by Pharmacia LKB Biotechnology Inc., Piscataway, N.J., U.S.A.). A 20-nucleotide target, with the sequence complementary to that of the anti-target segment of the probe, was similarly synthesized and purified. General methods for the performance of these manipulations are well known in the art and are described in, for example, Frank et al. (1981) Nucl. Acids Res. 9:4967–4979; Ogden and Adams (1987), Methods in Enzymology, 152:61–87; and Smith (1980) Methods in Enzymology, 65:371–380. The probe and target were stored frozen at −20° C. in sterile distilled water.

EXAMPLE 2

Figure 2:
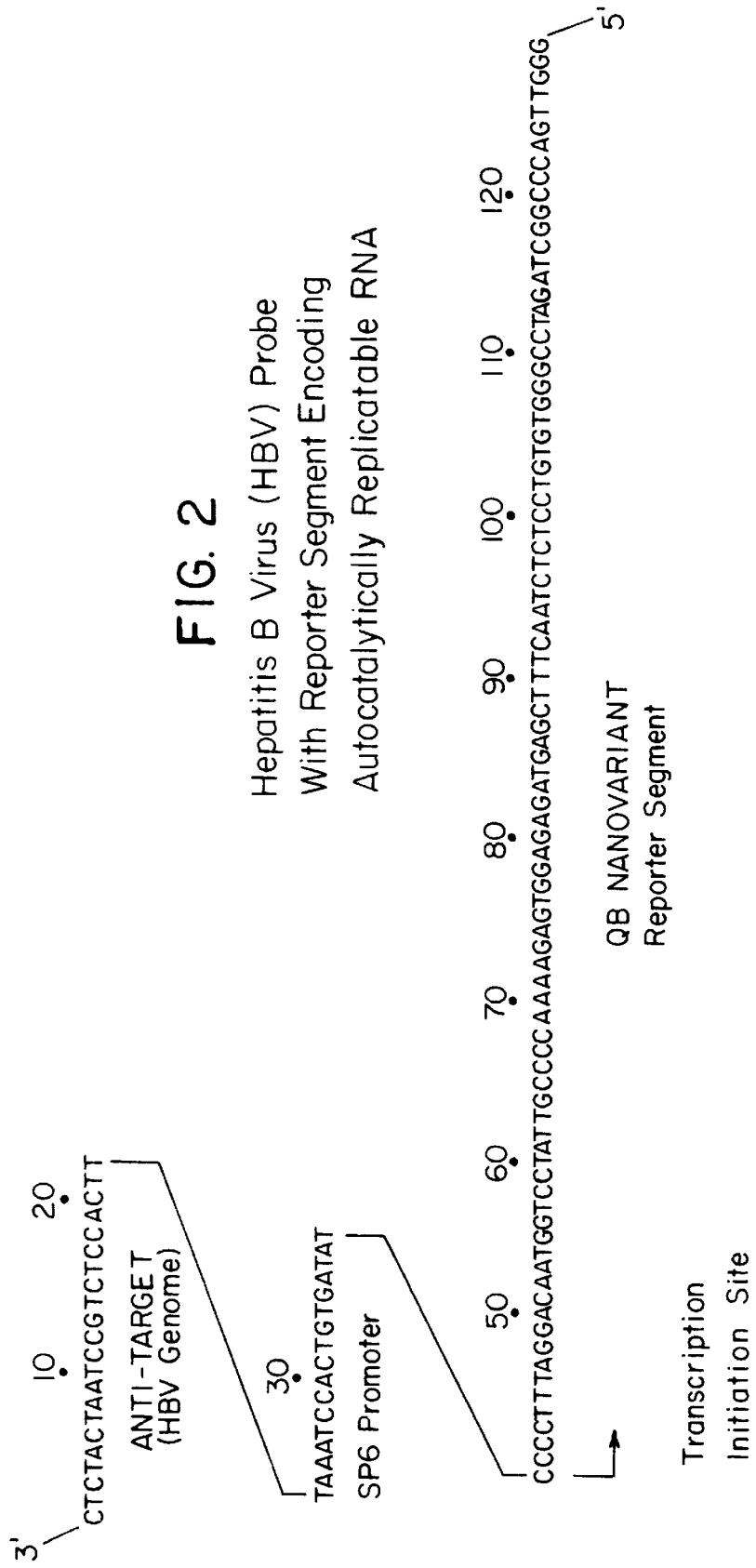
FIG. 2 shows the sequence of a particular probe in accordance with the invention.

A single-stranded DNA probe, which, like the probes of Examples 1 and 3, is useful for the detection of hepatitis B virus (HBV) and which consists of 129 nucleotides with the sequence SEQ ID NO:1, was prepared and purified as described in Example 1. This probe is illustrated in FIG. 2. The first, i.e., the anti-target, segment of this probe has 22 nucleotides in a sequence from the DR1 region of the hepatitis B virus genome. The anti-target segment will anneal to the naturally occurring, free 3'-end of the L-(−)-strand of the HBV genome. See, Tiollais et al. (1985) Nature 317:490; Pasek et al. (1979) Nature 282:575. The third segment of this probe, the probe's promoter segment, is the negative strand (template strand) of a promoter recognized by the RNA polymerase of bacteriophage SP6 and is oriented so that the template for transcription from the promoter, in the double-stranded DNA resulting from extension of target annealed to probe, is the fifth segment of the single-stranded probe. With reference to the SP6 promoter, see Brown et al. (1986), Nucl. Acids Res. 14:3521. In the double-stranded DNA resulting from extension of target annealed to probe, transcription from the SP6 promoter will start at the G:C pair corresponding to the C at position 40 in the probe as illustrated in FIG. 2. Apparently, the SP6 RNA polymerase requires a G in the coding strand at the transcriptional start site of DNAs transcribed by the enzyme from SP6 promoters; see Brown et al., supra. The rG at the 5'-end of the transcript made using SP6 RNA polymerase with the double-stranded DNA resulting from extension of target annealed to the probe of this example is the 5'-terminal nucleotide of the nanovariant (+) RNA (nv(+)RNA) corresponding to the nanovariant (−) RNA, of which the sequence is the same as that of the reporter segment of the single-stranded probe of this example. The fifth segment, i.e., the reporter segment, of the probe of this example has 90 nucleotides in the same sequence as the nanovariant (−) RNA reported by Schaffner et al. (1977), J. Mol. Biol. 135:917. This nanovariant (−) RNA is sometimes referred to herein as nv(−)RNA and is a template for autocatalytic replication by Qβ-replicase. In the probe of this example, both the first linker, joining the first and third segments, and the second linker, joining the third and fifth segments, are bonds between 5'-terminal phosphates and 3'-carbons of 3'-terminal nucleotides. The probe was stored frozen at −20° C. in sterile distilled water.

EXAMPLE 3

Figure 3:
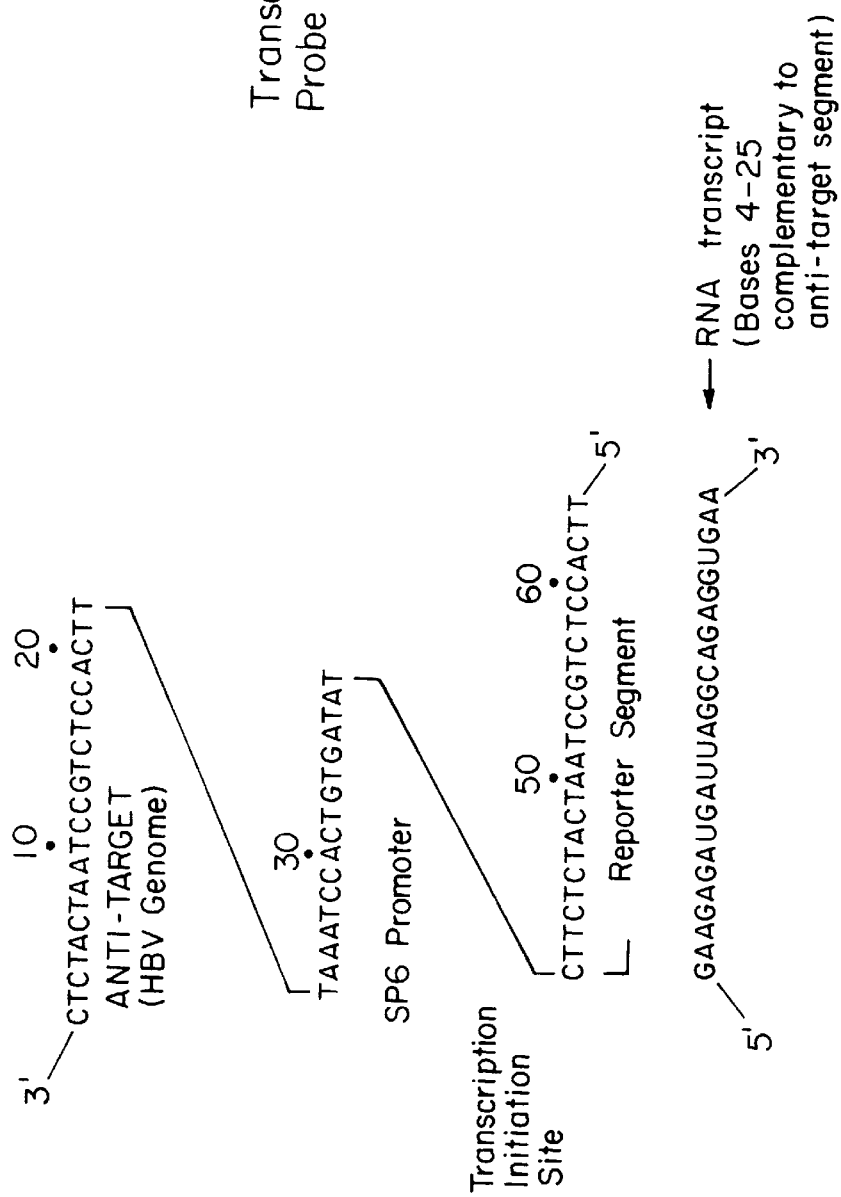
FIG. 3 shows the sequence of a particular probe in accordance with the invention.

A single-stranded DNA probe consisting of 64 nucleotides in the sequence of SEQ ID NO:2 was prepared and purified as described in Example 1. This probe is illustrated in FIG. 3. The first and third segments of this probe have the same sequences, are oriented with respect to each other in the same way, and are joined by the same first linker (a bond) as the probe of Example 2. The fifth segment (reporter segment) consists of two subsegments joined by a bond between the 5'-terminal phosphate of the subsegment at the 3'-end and the 3'-carbon of the 3'-terminal nucleotide of the subsegment at the 5'-end. The subsegment at the 3'-end is a trinucleotide with the sequence 5'-TTC and provides at the start of transcription in the double-stranded DNA resulting from chain extension of target hybridized to probe the three base pairs

5'-GAA
3'-CTT

The presence of these three base pairs adjacent the downstream end of the promoter in the double-stranded DNA may enhance the yield of transcript, as in most, if not all, occurrences in nature of the SP6 promoter, the transcribed DNA starts with the same three base pairs in the same sequence. See Brown et al., supra. The subsegment at the 5'-end of the fifth segment has the same sequence as the first (anti-target) segment of the probe. Thus, the transcript with the sequence of SEQ ID NO:3, made from the fifth segment as template in the double-stranded DNA resulting from chain extension of target hybridized to probe, can also serve as a "target" to prime chain extension along probe as template to make a double-stranded DNA, one strand of which consists of the third and fifth segments of the probe (and the bond between them) and from which additional transcript, with the sequence complementary to that of the fifth segment can be made. In the probe of this example, the second linker is a bond between the 5'-terminal phosphate of the third segment and the 3'-carbon of the 3'-terminal nucleotide of the fifth segment.

EXAMPLE 4

This example illustrates the performance of an assay method in accordance with the present invention utilizing the probe and target prepared in Example 1. A concentrated hybridization solution having a ten-fold excess of the 20-nucleotide target segment was prepared by combining 750 pm (picomoles) of target and 75 pm of probe in 5 μl of 1× SSC (7.5 mM NaCl; 0.75 mM Na citrate; pH 7.0). The solution was heated at 70° C. for 5 minutes, then cooled slowly for about an hour to 37° C., then chilled on ice and spun in a microcentrifuge for 10 seconds To prepare the double-stranded DNA, 10 μl reaction mixes were prepared which contained 0.5 μl of the concentrated probe-target hybridization solution (7.5 pm of probe); 1 mM of each DATP, dCTP, dGTP and dTTP; 20 mM KCl;

50 mM Tris-HCl (pH 8.3 at 42° C.); 10 mM MgCl$_2$; 15 mM NaCl; 10 mM dithiothreitol (DTT) and 3 units/$\mu$l AMV reverse transcriptase. The transcriptase was added last to the reaction solution, and then the mix was incubated at 42° C. for one hour. Solutions containing 7.5 pm of probe alone, 75 pm of target alone, and neither probe nor target were treated in the same manner and used as controls. As explained below, the extent of reverse transcriptase activity was determined by assaying the incorporation of 5'-[alpha-$^{32}$P] DATP into trichloroacetic acid (TCA)-precipitable material.

To prepare RNA transcripts, a sample of the double-stranded DNA prepared, as described in the previous paragraph, by chain extension of target hybridized to probe, was diluted directly into an RNA polymerase (transcription) reaction mix. A 20 $\mu$l reaction mix was prepared which consisted of 2 $\mu$l of the solution with double-stranded DNA prepared as described in the preceding paragraph; 2 mM each of rATP, rCTP, rGTP and rUTP; 40 mM Tris-HCl (pH 7.5); 10 mM MgCl$_2$; 15 mM NaCl; 2 mM spermidine; 10 mM DTT and 5 units/$\mu$l SP6 RNA polymerase. Reaction was initiated by the addition of enzyme and the reaction mix was then incubated for two hours at 37° C. Control reaction mixes were also prepared which containedrespectively 1.5 pm probe alone, 15 pm target alone, or neither probe nor target.

The products of the reactions catalyzed by the AMV reverse transcriptase and SP6 RNA polymerase were analyzed by electrophoresis and autoradiography. A sample of the radiolabelled, ethanol-precipitated products was denatured at 70° C. in Urea Blue Juice (10 M urea, 1 mM EDTA, 5% glycerol, 0.05% bromophenol blue, 0.05% xylene cyanole; 8M urea final concentration) and electrophoresed on a denaturing 7M urea, 10% polyacrylamide gel at about 55° C. and at 400 V (about 12.5 W, about 30 mamps) for 1 hour. The gel was then heat- and vacuum-dried, and placed and exposed on x-ray film, so that the migration of the products could be recorded and observed. Sizes were estimated based on the migration of oligo-sized standards included in adjacent lanes of the gel.

Results of the TCA precipitation of the reverse transcriptase products showed that 27.5 pmol of dNTP are incorporated per pmol of probe put into the reaction. Electrophoretic analysis of these extension products showed that they were full-length 132 mers. Thus, since each target should have been extended by 112 nucleotides, it was concluded that 24.6% (27.5/112) of the probe molecules originally put in the reaction acted as templates for the synthesis of the complementary extension of target. The background synthesis in the control reaction mixes containing only probe or only target was indistinguishable from control reaction mixes without both probe and target.

Analysis of the TCA-precipitated transcription products showed that there are 19,750 pmol rNTP incorporated per pmol probe in the reaction. Since each round of transcription by the SP6 RNA polymerase from the double-stranded DNA resulting from chain-extension of target hybridized to probe should have, and was observed to have, produced a transcript 93 nucleotides long, the probe molecules in the reaction each yielded, on the average, 212 (19,750/93) transcripts; thus, amplification of probe using only transcription resulted in a 212-fold amplification of probe. Electrophoretic analysis of the transcription products from the double-stranded DNA resulting from chain extension using probe as template of target hybridized to probe showed that they are full-length 93 mers. In contrast, analysis of the transcription products for control reaction mixes having only probe showed that the background synthesis comprised products which were predominantly less than 20 nucleotides long, although transcript that was apparently full-length was observed at a level of about 0.1% of the total precipitatable product made, apparently because the RNA polymerase is capable of initiating transcription at a low level from (−)-strand of promoter in single-stranded form.

EXAMPLE 5

For further amplification, by autocatalytic replication using Q$\beta$ replicase, of the RNA transcripts formed as in Example 4 using the probe of Example 2 and, as a target, a 20-nucleotide DNA in the sequence complementary to the sequence of the 20 nucleotides at the 3'-end of the probe of Example 2, an aliquot of a transcription reaction mix was sampled directly into a replication reaction mix. A 10 $\mu$l replication reaction mix was prepared which contained 0.79 pm transcription product, 2 mM each of rATP, rCTP, rGTP and rUTP; 40 mM Tris-HCl (pH 7.5); 13 mM MgCl$_2$; 0.1 $\mu$g/$\mu$l Q$\beta$-replicase. The replication reaction was initiated by the addition of the enzyme and the replication reaction mix was then incubated at 40° C. for one hour. A reaction mix which included no template was used as the negative control.

The amount of RNA synthesized in each reaction was determined by assaying the level of incorporation of 5'-[alpha-$^{32}$P] rCTP into TCA-precipitable material. A total of 9953.4 pm of rNTP were incorporated into product in the 10 $\mu$l reaction, which contained 0.79 pm of transcript as template. No incorporation was observed in the negative control.

EXAMPLE 6

A probe with the sequence shown in SEQ ID NO:6, was prepared and purified by the methods described in Example 1 with, at the 3'-end, a 40-mer anti-target segment of sequence 3'-CGAGCTCCCC GGGATCCGGA GATCTC-CTAG GTCGACACGT, SEQ ID NO:4, joined by a bond to the 5'-phosphate of the anti-target segment a promoter segment of sequence 3'-ATTATGCTGA GTGATAT, SEQ ID NO:5, and, at the 5'-end and joined by a bond to the 5'-phosphate of the promoter segment a 91-nucleotide reporter segment which has the same sequence as the reporter segment shown in FIG. 2 except that the hexanucleotide at the 3'-end has the sequence 3'-CCCTCT rather than 3'-CCCCTT and there is a T added at the 5'-end. The third segment (promoter segment) of 17 nucleotides is the negative strand of a promoter recognized by the RNA polymerase of bacteriophage T7 and has the sequence complementary to the so-called "consensus sequence" of the T7 promoter. The 40-nucleotide DNA with the sequence complementary to that of the anti-target segment of the probe was also made and purified as described in Example 1. Following the procedures described in the previous examples, with the probe and 40 nucleotide target of this example, but using T7 RNA polymerase (at 500 units/ml) in place of SP6 RNA polymerase to catalyze transcription, it was found that 186 transcripts, of 91 nucleotide each, were made for each molecule of double-stranded DNA made by AMV reverse transcriptase-catalyzed primer extension of target annealed to probe.

While the present invention has now been described and exemplified with some specificity, those skilled in the art will appreciate the various modifications and variations that may be made in what has been described without departing from the spirit of the invention. It is intended that these modifications and variations also be encompassed by the present invention and that the scope of the present invention be limited solely by the broadest interpretation that lawfully can be accorded the appended claims.

We claim:

1. A single-stranded DNA probe comprising the following in 3'- to 5'-order:
   (a) an antitarget nucleic acid segment capable of hybridizing to a target nucleic acid segment;
   (b) a (−)-promoter segment functionally linked to the antitarget segment such that hybridization of the antitarget segment to the taraet segment results in the capability of extending the target segment utilizing the (−)-promoter segment as a template, such that the (−)-promoter becomes a double-stranded promoter via chain extension, wherein the double-stranded promoter is capable of being recognized and bound by a DNA-dependent RNA polymerase; and
   (c) a nucleic acid reporter segment, having a subsegment with the same sequence as a subsegment of the antitarget nucleic acid segment, the subsegment having sufficient length to allow a transcript thereof to hybridize to the antitarget nucleic acid segment, wherein the reporter segment is functionally linked to the (−)-promoter segment such that the reporter segment is capable of being transcribed under control of the double-stranded promoter.

2. A probe according to claim 1, wherein the probe is shorter than 200 nucleotides.

3. A probe according to claim 1, wherein the (−)-promoter segment is a strand of a promoter recognized by the RNA polymerase of a bacteriophage selected from the group consisting of T3 phage, T7 phage, and SP6 phage.

4. A test kit for detecting the presence of a target nucleic acid segment in a sample, the kit comprising:
   (a) a single-stranded DNA probe comprising the following in 3'- to 5'-order:
      (1) an antitarget nucleic acid segment capable of hybridizing to a target nucleic acid segment;
      (2) a (−)-promoter segment functionally linked to the antitarget segment such that hybridization of the antitarget segment to the target segment results in the capability of extending the target segment utilizing the (−)-promoter segment as a template, such that the (−)-promoter segment becomes a double-stranded promoter via chain extension, wherein the doublestranded promoter is capable of being recognized and bound by a DNA-dependent RNA polymerase; and (3) a nucleic acid reporter segment, having a subsegment with the same sequence as a subsegment of the antitarget nucleic acid segment, the subsegment having sufficient length to allow a transcript thereof to hybridize to the antitarget nucleic acid segment, the reporter segment functionally linked to the (−)-promoter segment such that the reporter segment is capable of being transcribed under control of the double-stranded promoter; and (b) an enzyme with DNA polymerase activity.

5. The test kit of claim 4, wherein the (−)-promoter segment is a strand of a promoter recognized by the RNA polymerase of a bacteriophage selected from the group consisting of T3 phage, T7 phage, and SP6 phage.

6. The test kit of claim 4 additionally comprising an RNA polymerase which recognizes, for initiation of transcription, a double stranded DNA promoter segment which includes the (−)-promoter segment of the probe.

7. The test kit of claim 4, wherein the probe is shorter than 200 nucleotides in length.

8. The test kit of claim 4, wherein the enzyme with DNA polymerase activity is AMV reverse transcriptase.

9. A test kit for detecting the presence of a target nucleic acid segment in a sample, the kit comprising:

(a) a single-stranded DNA probe that is shorter than 200 nucleotides in length, comprising the following in 3'- to 5'-order:

(1) an antitarget nucleic acid segment capable of hybridizing to a target nucleic acid segment;

(2) a (−)-promoter segment that is a strand of a promoter recognized by the RNA polymerase of a bacteriophage selected from the group consisting of T3 phage, T7 phage, and SP6 phage, the (−)-promoter segment functionally linked to the antitarget segment such that hybridization of the antitarget segment to the target segment results in the capability of extending the target segment utilizing the (−)-promoter segment as a template, such that the (−)-promoter segment becomes a double-stranded promoter via chain extension, wherein the double-stranded promoter is capable of being recognized and bound by a DNA-dependent RNA polymerase; and (3) a nucleic acid reporter segment, having a subsegment with the same sequence as a subsegment of the antitarget nucleic acid segment, the subsegment having sufficient length to allow a transcript thereof to hybridize to the antitarget nucleic acid segment, the reporter segment functionally linked to the (−)-promoter segment such that the reporter segment is capable of being transcribed under control of the double-stranded promoter;

(b) an enzyme with DNA polymerase activity; and (c) an RNA polymerase which recognizes, for initiation of transcription, the double-stranded DNA promoter segment.

10. A test kit for detecting the presence of a target nucleic acid segment in a sample, the kit comprising:

(a) a probe, for detecting the presence of a target nucleic acid segment in a sample, comprising:

(1) a first single-stranded DNA molecule comprising the following in 3'- to 5'-order:

(i) a first antitarget nucleic acid segment capable of hybridizing to the target nucleic acid segment;

(ii) a first (−)-promoter segment functionally linked to the first antitarget segment such that hybridization of the first antitarget segment to the first target segment results in the capability of extending the target segment utilizing the first (−)-promoter segment as a template, such that the first (−)-promoter segment becomes a first double-stranded promoter via chain extension, wherein the first double-stranded promoter is capable of being recognized and bound by a DNA-dependent RNA polymerase; and (iii) a first nucleic acid reporter segment functionally linked to the first (−)-promoter segment such that first reporter segment is capable of being transcribed under control of the first double-stranded promoter to produce a second target segment;

(2) a second single-stranded DNA molecule comprising the following in 3'- to 5'-order:

(i) a second antitarget nucleic acid segment;

(ii) a second (−)-promoter segment functionally linked to the second antitarget segment such that hybridization of the second antitarget segment to the second target segment results in the capability of extending the second target segment utilizing the second (−)-promoter segment as a template such that the second (−)-promoter segment becomes a second double-stranded promoter via chain extension, wherein the second double-stranded promoter is capable of being recognized and bound by a DNA-dependent RNA polymerase; and (iii) a second nucleic acid reporter segment functionally linked to the second (−)-promoter segment such that second reporter segment is capable of being transcribed under control of the second double-stranded promoter; and (b) an enzyme with DNA polymerase activity.

11. The test kit of claim 10, wherein each of the first and second (−)-promoter segments is a strand of a promoter recognized by the RNA polymerase of a bacteriophage selected from the group consisting of T3 phage, T7 phage, and SP6 phage.

12. The test kit of claim 10 additionally comprising first and second RNA polymerases which recognize, for initiation of transcription, the first and second (−)-promoter segments, respectively.

13. The test kit of claim 10, wherein each of the first and second DNA molecules is shorter than 200 nucleotides in length.

14. The test kit of claim 10, wherein the enzyme with DNA polymerase activity is AMV reverse transcriptase.

15. A test kit for detecting the presence of a target nucleic acid segment in a sample, the kit comprising:

(a) a probe, for detecting the presence of a target nucleic acid segment in a sample, comprising:

(1) a first single-stranded DNA molecule, 200 or less nucleotides in length, comprising the following in 3'- to 5'-order:

(i) a first antitarget nucleic acid segment capable of hybridizing to the target nucleic acid segment;

(ii) a first (−)-promoter segment that is a strand of a promoter capable of being recognized by a RNA polymerase of a bacteriophage selected from the group consisting of T3 phage, T7 hage, and SP6 phage, the first (−)-promoter segment functionally linked to the first antitarget segment such that hybridization of the first antitarget segment to the first target segment results in the capability of extending the target segment utilizing the first (−)-promoter segment as a template such that the first (−)-promoter segment becomes a first double-stranded promoter via chain extension, wherein the first double-stranded promoter is capable of being recognized and bound by a DNA-dependent RNA polymerase; and (iii) a first nucleic acid reporter segment functionally linked to the first (−)-promoter segment such that first reporter segment is capable of being transcribed under control of the first double-stranded promoter to produce a second target segment;

(2) a second single-stranded DNA molecule, 200 or less nucleotides in length, comprising the following in 3'- to 5'-order:

(i) a second antitarget nucleic acid segment;

(ii) a second (−)-promoter segment that is a strand of a promoter capable of being recognized by a RNA polymerase of a bacteriophage selected from the group consisting of T3 phage, T7 phage, and SP6 phage, the second (−)-promoter functionally linked to the second antitarget segment such that hybridization of the second antitarget segment to the second target segment results in the capability of extending the second target segment utilizing the second (−)-promoter segment as a template such that the second (−)-promoter segment becomes a second double-stranded promoter via chain extension, wherein the second double-stranded promoter is capable of being recognized and bound by a DNA-dependent RNA polymerase; and (iii) a second nucleic acid reporter segment functionally linked to the second (−)-promoter segment such that second reporter segment is capable of being transcribed under control of the second double-stranded promoter; and (b) an enzyme with DNA polymerase activity;

(c) an RNA polymerase which recognizes, for initiation of transcription, the first double-stranded promoter; and (d) an RNA polymerase which recognizes, for initiation of transcription, the second double-stranded promoter.

16. A method of testing a sample of nucleic acid for the presence of a target nucleic acid segment, the method comprising:

(a) combining the nucleic acid of the sample with a DNA probe under conditions, whereby, if the target nucleic acid segment is present in the sample, the probe anneals to the target segment, the probe comprising the following in 3'- to 5'-order:

(1) an antitarget nucleic acid segment capable of hybridizing to the target nucleic acid segment;

(2) a (−)-promoter segment which, when double stranded, is recognized and bound by a DNA-dependent RNA polymerase; and (3) a nucleic acid reporter segment, having a subsegment with the same sequence as a subsegment of the antitarget nucleic acid segment, which is capable of being transcribed under control of a double stranded promoter;

(b) combining the product of step (a) with an enzyme having DNA polymerase activity under conditions whereby the target nucleic acid, which is annealed to the probe and which has a hydroxyl group at its 3'-terminus, primes DNA synthesis using the (−)-promoter segment of the probe as a template to yield a double stranded DNA segment wherein the (−)-promoter segment is a portion of the double stranded segment;

(c) combining the product of step (b) with an RNA polymerase, which recognizes for initiation of transcription the promoter of the double stranded segment which is the product of step (b), under conditions whereby RNA that is complementary to the reporter segment is transcribed from the double stranded segment; and (d) ascertaining whether RNA that is complementary to the reporter segment was produced in step (c), thereby detecting the target nucleic acid segment in the sample.

17. The method of claim 16, wherein the method further comprises the step of treating the nucleic acid of the sample, prior to or following step (a), so that at least a portion of the target nucleic acid annealed to the probe is a 3'-terminal segment of nucleic acid and has a hydroxyl group at its 3'-terminus.

18. The method of claim 16, wherein the (−)-promoter segment is a strand of a promoter recognized by the RNA polymerase of a bacteriophage selected from the group consisting of T3 phage, T7 phage, and SP6 phage.

19. The method of claim 16, wherein the DNA probe is shorter than 200 nucleotides.

20. The method of claim 16, wherein the enzyme with DNA polymerase activity is AMV reverse transcriptase.

21. A method of testing a sample of nucleic acid for the presence of a target nucleic acid segment, the method comprising:

(a) combining the nucleic acid of the sample with a DNA probe under conditions, whereby, if the target nucleic acid segment is present in the sample, the probe anneals to the target segment, the probe comprising the following in 3'- to 5'-order:

(1) an antitarget nucleic acid segment capable of hybridizing to the target nucleic acid segment;

(2) a (−)-promoter segment which, when double stranded, is recognized and bound by a DNA-dependent RNA polymerase; and (3) a nucleic acid reporter segment which is capable of being transcribed under control of a double stranded promoter;

(b) treating the nucleic acid of the sample, prior to or following step (a), so that at least a portion of the target nucleic acid annealed to the probe is the 3'-terminal segment of nucleic acid and has a hydroxyl group at its 3' terminus;

(c) combining the products of steps (a) and (b) together with an enzyme having DNA polymerase activity under conditions whereby the target nucleic acid, which is annealed to the probe and which has a hydroxyl group at its 3'-terminus, primes DNA synthesis using the (−)-promoter segment of the probe as a template to yield a double stranded DNA segment wherein the (−)-promoter segment is a portion of the double stranded segment;

(d) combining the product of step (c) with an RNA polymerase, which recognizes for initiation of transcription the promoter of the double stranded segment which is the product of step (c), under conditions whereby RNA that is complementary to the reporter segment is transcribed from the double stranded segment; and (e) ascertaining RNA that is complementary to the reporter segment was produced in step (d), thereby detecting the target nucleic acid segment in the sample.

22. The method of claim 21, wherein the (−)-promoter segment is a strand of a promoter recognized by the RNA polymerase of a bacteriophage selected from the group consisting of T3 phage, T7 phage, and SP6 phage.

23. The method of claim 21, wherein the DNA probe is shorter than 200 nucleotides.

24. The method of claim 21, wherein the reporter segment encodes the segment of an RNA that is autocatalytically replicatable by Qβ replicase and wherein the kit contains Qβ replicase.

25. The method of claim 21, wherein the enzyme with DNA polymerase activity is AMV reverse transcriptase.

26. A method of testing a sample of nucleic acid for the presence of a target nucleic acid segment, the method comprising:
(a) combining the nucleic acid of the sample with a DNA probe under conditions, whereby, if the target nucleic acid segment is present in the sample, a first DNA molecule anneals to the target segment, the probe comprising:
(1) the first DNA molecule comprising the following in 3'- to 5'-order:
(i) a first antitarget nucleic acid segment capable of hybridizing to the target nucleic acid segment;
(ii) a first (−)-promoter segment which, when double stranded, is recognized and bound by a DNA-dependent RNA polymerase; and
(iii) a first nucleic acid reporter segment which is capable of being transcribed under control of a double stranded promoter;
(2) a second DNA molecule comprising the following in 3'- to 5'-order:
(i) a second antitarget nucleic acid segment having a subsegment with the same sequence as a subsegment of the first reporter segment;
(ii) a second (−)-promoter segment which, when double stranded, is recognized and bound by a DNA-dependent RNA polymerase; and
(iii) a second nucleic acid reporter molecule which is capable of being transcribed under control of a double stranded promoter;
(b) combining with the product of step (a) an enzyme having DNA polymerase activity under conditions whereby the target nucleic acid, which is annealed to the first DNA molecule and which has a hydroxyl group at its 3'-terminus, primes DNA synthesis using the (−)-promoter segment of the first DNA molecule as a template to yield a first double stranded DNA segment wherein the first (−)-promoter segment is a portion of the double stranded segment;
(c) combining with the product of step (b) an RNA polymerase, which recognizes for initiation of transcription the promoter of the first double stranded segment which is the product of step (b), under conditions whereby an RNA transcript that is complementary to the first reporter segment is transcribed from the double stranded segment;
(d) combining with the product of step (c) an enzyme having DNA polymerase activity under conditions whereby the RNA transcript that is complementary to the first reporter segment, which is annealed to the second antitarget nucleic acid segment, which has a hydroxyl group at its 3'-terminus, primes DNA synthesis using the second (−)-promoter segment of the second DNA molecule as a template to yield a second double stranded DNA segment wherein the second (−)-promoter segment is a portion of the second double stranded segment;
(e) combining with the product of step (d) an RNA polymerase, which recognizes for initiation of transcription the promoter of the second double stranded segment which is the product of step (d), under conditions whereby RNA that is complementary to the reporter segment is transcribed from the double stranded segment; and
(f) ascertaining RNA that is complementary to the second reporter segment was produced in step (e), thereby detecting the target nucleic acid segment in the sample.

27. The method of claim 26, wherein the method further comprises the step of treating the nucleic acid of the sample, prior to or following step (a), so that at least a portion of the target nucleic acid annealed to the probe is the 3'-terminal segment of nucleic acid and has a hydroxyl group at its 3'-terminus.

28. The method of claim 26, wherein each of the first and second (−)-promoter segments is a strand of a promoter recognized by the RNA polymerase of a bacteriophage selected from the group consisting of T3 phage, T7 phage, and SP6 phage.

29. The method of claim 26, wherein each of the first and second DNA molecules is shorter than 200 nucleotides.

30. The method of claim 26, wherein the enzyme with DNA polymerase activity is AMV reverse transcriptase.

* * * * *

UNITED STATES PATENT AND TRADEMARK OFFICE
CERTIFICATE OF CORRECTION

PATENT NO.   : 6,100,024
DATED        : August 8, 2000
INVENTOR(S)  : Hudson et al.

Page 1 of 1

It is certified that error appears in the above-identified patent and that said Letters Patent is hereby corrected as shown below:

Column 15,
Line 20, delete "D-Gel®" and insert in its place -- D-Gel™ --.

Column 16,
Line 67, delete "DATP," and insert in its place dATP, --.

Column 17,
Line 9, delete "DATP" and insert in its place dATP --.
Line 22, delete "containedrespectively" and insert in its place -- contained respectively --.

Column 21,
Line 54, delete "taraet" and insert in its place -- target --.

Column 24, claim 15,
Line 64, delete "hage" and insert in its place -- phage --.

Signed and Sealed this

Eighteenth Day of December, 2001

Attest:

Attesting Officer

JAMES E. ROGAN
*Director of the United States Patent and Trademark Office*